United States Patent [19] [11] 4,417,055
Nishiyama et al. [45] Nov. 22, 1983

[54] PROCESS FOR PRODUCING A β-TRIFLUOROMETHYLPYRIDINE

[75] Inventors: Ryuzo Nishiyama, Takatsuki; Kanichi Fujikawa, Moriyama; Isao Yokomichi, Moriyama; Yasuhiro Tsujii, Moriyama; Shigeyuki Nishimura, Shiga, all of Japan

[73] Assignee: Ishihara Sangyo Kaisha Ltd., Osaka, Japan

[21] Appl. No.: 356,528

[22] Filed: Mar. 9, 1982

[30] Foreign Application Priority Data

Mar. 27, 1981 [JP] Japan ................................. 56-44851

[51] Int. Cl.³ ............................................. C07D 213/26
[52] U.S. Cl. ..................................... 546/345; 546/346
[58] Field of Search ................................ 546/345, 346

[56] References Cited

U.S. PATENT DOCUMENTS 4,259,496 3/1981 Whitaker et al. ................... 546/345
4,266,064 5/1981 Nishiyama et al. ................. 546/345
4,288,599 9/1981 Nishiyama et al. ................. 546/345

Primary Examiner—Alan L. Rotman
Attorney, Agent, or Firm—Oblon, Fisher, Spivak, McClelland & Maier

[57] ABSTRACT

A pyridine derivative having the formula

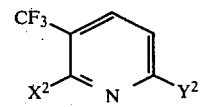

wherein $X^2$ and $Y^2$ represents hydrogen atom or chlorine atom is produced by reacting a pyridine compound having the formula

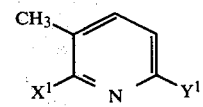

wherein $X^1$ and $Y^1$ represent hydrogen atom or chlorine atom, with chlorine and anhydrous hydrogen fluoride by a vapor phase reaction in the presence of a catalyst at a temperature of 250° to 600° C. using as the catalyst a fluoride of a metal selected from the group consisting of copper, vanadium, tin, bismuth, zirconium, magnesium, barium, zinc, calcium, potassium and sodium.

10 Claims, No Drawings

PROCESS FOR PRODUCING A β-TRIFLUOROMETHYLPYRIDINE

BACKGROUND OF THE INVENTION

1. Field of the Invention

The present invention relates to a process for producing β-trifluoromethylpyridines directly from β-picoline or a chloro β-picoline, in particular, a process for producing β-trifluoromethylpyridines (hereinafter referring to as β-TFP$_s$) by a vapor phase reaction of β-picoline or a chloro β-picoline with chlorine and anhydrous hydrogen fluoride in the presence of a special catalyst.

2. Description of the Prior Art

β-TFP$_s$ are compounds useful as intermediates for dyes, medicines or agricultural chemicals such as herbicides and insecticides. The industrial values of these compounds are significant recently.

As the process for producing the β-TFP$_s$, it has been known that chlorine gas is fed into a solution of β-picoline in carbon tetrachloride under an irradiation of ultraviolet rays to produce β-trichloromethylpyridines, and the β-trichloromethylpyridines are reacted with anhydrous hydrogen fluoride or antimony trifluoride by a liquid phase reaction. However, this process requires a long time for the reaction and produces a large quantity of by-products to be a low yield. Therefore, it is not satisfactory as an industrial process.

The present inventors discovered a process for producing β-TFP$_s$ by a vapor phase reaction of β-picoline or chloro β-picolines with chlorine and anhydrous hydrogen fluoride in the presence of a certain fluoride of metallic element and diluent. They also gained the discovery that this process was able to provide the object product in a single step and for short time to resolve the defects of said conventional process, and proposed patent application of British Patent Publication 2045245.

SUMMARY OF THE INVENTION

They have gained the discovery that in the process for producing β-TFP$_s$ by said vapor phase reaction, special fluorides of metallic element show favorable catalytic activity. They have been selected from the many metallic fluorides.

The present invention relates to the following, that is, in a process for producing a β-trifluoromethylpyridine having the formula

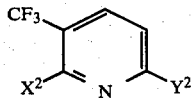

wherein $X^2$ and $Y^2$ represent hydrogen atom or chlorine atom, which comprises reacting a pyridine compound having the formula

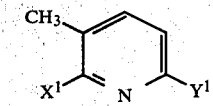

wherein $X^1$ and $Y^1$ represent hydrogen atom or chlorine atom, with chlorine and anhydrous hydrogen fluoride by a vapor phase reaction in the presence of a catalyst, at a temperature of 250° to 600° C., an improvement characterized by using as the catalyst a fluoride of an element selected from the group consisting of copper, vanadium, tin, bismuth, zirconium, magnesium, barium, zinc, calcium, potassium and sodium.

The pyridine compounds used in the present invention include β-picoline and chloro β-picolines such as 2-chloro-β-picoline, 6-chloro-β-picoline and 2,6-dichloro-β-picoline. Especially, β-picoline is easily available as a starting material in various organic syntheses. In accordance with the present invention, the chloro β-trifluoromethylpyridines can be directly produced from this compound. This is remarkably advantageous.

DETAILED DESCRIPTION OF THE PREFERRED EMBODIMENTS

The fluorides of metallic element which are used as the catalyst in the present invention are exemplified as follows, for example, sodium fluoride, potassium fluoride, cuprous fluoride, cupric fluoride, magnesium fluoride, calcium fluoride, barium fluoride, zinc fluoride, zirconium fluoride, stannous fluoride, stannic fluoride, vanadium trifluoride, vanadium tetrafluoride, vanadium pentafluoride, bismuth fluoride. It is preferable to use a copper fluoride, a vanadium fluoride or a tin fluoride and more preferable to use a copper fluoride as the catalyst. Said fluoride of metallic element may be used separately or in combination.

This catalyst is mixed usually with a carrier such as active carbon, active alumina or aluminum trifluoride to form granules or pellets having suitable size. This is used as a fixed bed or a fluidized bed. The catalyst can be placed in a reaction tube by charging the metallic fluoride itself. In an industrial process, it is preferable to charge said metallic oxides, halides except for fluorides, oxyhalides, hydroxides, sulfides, sulfates, nitrates, phosphates or carbonates, or hydrates of said materials into the reaction tube and convert them into the fluorides by reacting them with anhydrous hydrogen fluoride.

The diluents can be organic solvent of halo-hydrocarbons such as F-112 (CFcl$_2$.CFcl$_2$) or F-113 (CF$_2$cl.CFcl$_2$), and inert gases such as nitrogen, helium or argon. The diluents have the functions for controlling a combustion, a carbonization and a formation of tarry by-products.

In the process of the present invention, the starting material and diluent can be separately fed into a reactor or can be fed as a mixture thereof. For example, the pyridine compound as the starting material is fed after vaporizing it or dissolving it in an organic solvent and vaporizing the mixture. Anhydrous hydrogen fluoride is fed after vaporizing it. The reaction is carried out after mixing these components with chlorine or diluent in the feeding step.

Amounts of chlorine and anhydrous hydrogen fluoride are not critical and depending on a kind of the pyridine compound, a kind of the object compound and a reactor, and are respectively in ranges of 2 to 15 moles and 2 to 60 moles based on 1 mole of the pyridine compound. An amount of diluent is usually in a range of 3 to 70 moles based on 1 mole of the pyridine compound. A reaction temperature is usually in a range of 250° to 600° C., preferably 250° to 500° C. and a residence time of the reaction mixture in the reaction zone is usually in a range of 0.5 to 50 seconds. In usual, gaseous materials containing the fluorinated products such as β-TFP$_s$ of the main products and the unreacted hydrogen fluoride and chlorine, intermediates, hydrogen chloride as a by-product and diluent are discharged from the reactor.

β-TFP$_s$ are separated as a liquid mixture through a desired cooling and condensing device. The liquid mixture usually contains 3-trifluoromethylpyridine, 2-chloro-5-trifluoromethyl-pyridine, 2-chloro-3-trifluoromethylpyridine, 2,6-dichloro-3-trifluoromethylpyridine and so on.

When intermediates which are not converted into β-TFP$_s$ are remained in the liquid mixture, the intermediate can be recycled to the reaction zone after separating and recovering them together unreacted starting material or diluent. The resulting β-TFP$_s$ can be purified by the conventional purifying treatment such as an extraction, a distillation or a crystallization whereby a single compound of β-TFP$_s$ such as 2-chloro-5-trifluoromethylpyridine having high purity can be obtained.

The present invention will be further illustrated by certain examples, however, it is not limited by the description of the examples.

EXAMPLES 1 TO 6

An Inconel reaction tube with a fluidized bed of catalyst having a reaction zone of an inner diameter of 30 mm and a height of 500 mm was used as a reactor. Two Inconel preheating tube having an inner diameter of 20 mm and a length of 400 mm were jointed with the reaction tube to use for a preheating of starting materials and diluent. The reaction tube and preheating tube were covered by each electric heater and each insulator so as to control the temperature.

Material containing one mole of each metallic halide except for fluoride, oxyhalide, oxide or carbonate in 2.0 kg of aluminum trifluoride having granular diameter of 105 to 250μ was charged into the catalyst packing part and the reaction tube was heated at 175° C. Anhydrous hydrogen fluoride was fed at a ratio of 10 l/min. for about one hour to activate it. However, the mixture of 3% by weight of bismuth compound based on one mole of copper compound was used in the example 6 after treating it by the same manner.

The reaction tube was heated at the predetermined temperature. Then, 0.7 g/min. of β-picoline and 1.0 l/min. of nitrogen gas which were preheated at 250° C. were fed into the reaction tube as a mixture gas and 1.0 l/min. of chlorine gas and 0.8 l/min. of anhydrous hydrogen fluoride which were preheated at 250° C. were fed into the reaction tube as a mixture gas, and the reaction was carried out at the same ratio for about 4 hours. The residence time of reaction mixture in the reaction tube was about 3 seconds.

The gas discharged from the reaction tube was condensed by passing it through a water washing tower and an alkali washing tower. The oil was separated and neutralized by an ammonia aqueous solution to obtain oily product by a steam distillation. The oily product obtained by each reaction was analyzed by a hot gas chromatography. The result is shown in the table No. 1.

In the table, abbreviation of product shows the aftermentioned material. It is adapted also to the following table No. 2 and No. 3.
TF: 3-trifluoromethylpyridine
CTF: 2-chloro-5-trifluoromethylpyridine
2-CTF: 2-chloro-3-trifluoromethylpyridine
DCTF: 2,6-dichloro-3-trifluoromethylpyridine
other components:
Total percentage of compounds such as β-perchlorofluoro- or trifluoromethylpyridine having chlorine atom on pyridine nucleus.

TABLE NO. 1

| Exp. | Catalyst | Reaction temperature (°C.) | Yield of oily product (g) | Content (%) | | | | |
|---|---|---|---|---|---|---|---|---|
| | | | | CTF | 2-CTF | DCTF | TF | Other components |
| 1 | CuF$_2$ | 400 | 300 | 54.7 | 8.9 | 10.1 | 9.0 | 17.3 |
| 2 | CuF$_2$ | 410 | 300 | 55.6 | 9.4 | 13.0 | 3.7 | 18.3 |
| 3 | CuF$_2$ | 430 | 290 | 47.4 | 10.0 | 16.5 | 1.5 | 24.6 |
| 4 | VF$_5$ | 400 | 300 | 58.1 | 9.9 | 5.0 | 10.4 | 16.6 |
| 5 | SnF$_2$ | 400 | 300 | 53.2 | 10.2 | 7.9 | 15.0 | 13.7 |
| 6 | CuF$_2$ + BiF$_3$ | 410 | 300 | 56.5 | 9.1 | 12.1 | 4.3 | 17.9 |

EXAMPLES 7 TO 9

In accordance with the processes of Examples 1 to 6 except for changing 1.0 l/min. of chlorine gas to 1.2 l/min. and reaction temperature to 300° C., each reaction was carried out to obtain about 250 g. to 300 g. of the oily products. The oily product obtained in each reaction was analyzed by a hot gas chromatography. The result is shown in the table No. 2.

TABLE NO. 2

| Example | Catalyst | Content (%) | | | | |
|---|---|---|---|---|---|---|
| | | CTF | 2-CTF | DCTF | TF | Other components |
| 7 | CuF$_2$ | 21.7 | 6.2 | 1.0 | 57.9 | 13.2 |
| 8 | CuF | 21.4 | 5.3 | 1.2 | 48.9 | 23.2 |
| 9 | BiF$_3$ | 12.3 | 2.9 | 0.4 | 66.9 | 17.5 |
| 10 | SnF$_2$ | 20.1 | 6.7 | 0.2 | 41.7 | 31.3 |
| 11 | ZrF$_4$ | 24.2 | 4.3 | 1.3 | 41.2 | 29.0 |
| 12 | VF$_4$ | 24.6 | 6.5 | 0.3 | 47.0 | 21.6 |
| 13 | MgF$_2$ | 15.9 | 5.6 | 0.2 | 53.3 | 25.0 |
| 14 | BaF$_2$ | 13.8 | 3.5 | 0.5 | 57.1 | 25.1 |
| 15 | ZnF$_2$ | 11.1 | 3.0 | 0.6 | 56.0 | 29.3 |
| 16 | CaF$_2$ | 9.8 | 2.9 | 0.3 | 53.7 | 33.3 |
| 17 | KF | 4.9 | 1.9 | 0.2 | 21.7 | 71.3 |
| 18 | NaF | 4.4 | 1.9 | 0.2 | 23.5 | 70.0 |
| 19 | CuF$_2$ + BiF$_3$ | 20.6 | 4.3 | 1.0 | 62.1 | 12.0 |

In accordance with the processes of Examples 7 to 19 except for changing aluminium trifluoride as carrier to active carbon, the reaction and purification were carried out to obtain effects of catalyst by said fluorides of metallic elements.

EXAMPLE 20

In accordance with their processes of Examples 1 to 6 except for using 0.6 l/min. of chlorine gas, 0.8 l/min. of anhydrous hydrogen fluoride, about 3.5 seconds of residence time and 430° C. of reaction temperature, the reaction for 30 minutes and purification were carried out. The oily product was analyzed by a hot gas chromatography to obtain the result in the table No. 3.

TABLE NO. 3

| | | Content (%) | | | | |
|---|---|---|---|---|---|---|
| Example | Catalyst | CTF | 2-CTF | DCTF | TF | Other components |
| 20 | CuF$_2$ | 40.7 | 11.5 | 5.5 | 18.3 | 24.0 |

What is claimed is:

1. A process for producing a pyridine derivative having the formula

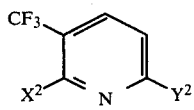

wherein $X^2$ and $Y^2$ represents hydrogen atom or chlorine atom, which comprises reacting a pyridine compound having the formula

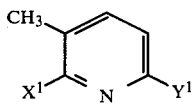

where $X^1$ and $Y^1$ represent hydrogen atom or chlorine atom with chlorine and anhydrous hydrogen fluoride by a vapor phase reaction in the presence of a catalyst at a temperature of 300° C. to 430° C. wherein, the catalyst is a fluoride of a metal selected from the group consisting of copper, vanadium, tin, bismuth, zirconium, magnesium, barium, zinc, calcium, potassium and sodium.

2. A process according to claim 1 wherein said catalyst is a copper fluoride, a vanadium fluoride or a tin fluoride.

3. A process according to claim 1 wherein said catalyst is a copper fluoride.

4. A process according to claim 1 wherein said reaction is carried out in the presence of a diluent.

5. A process according to claim 1 wherein said reaction is carried out at 400° C. to 430° C.

6. A process according to claim 1 wherein the residence time of the reaction mixture in the reaction zone is from 0.5 to 50 seconds.

7. A process according to claim 1 wherein said pyridine compound is β-picoline and said pyridine derivative is β-trifluoromethylpyridine, 2-chloro-3-trifluoromethylpyridine, 2-chloro-5-trifluoromethylpyridine or 2,6-dichloro-3-trifluoromethylpyridine.

8. A process according to claim 1 wherein said pyridine derivative is 2-chloro-5-trifluoromethylpyridine.

9. A process according to claim 1 wherein said pyridine derivative is β-trifluoromethylpyridine.

10. A process according to claim 1 wherein the catalyst is suspended in a gas flow containing the reaction mixture to carry out said reaction in a fluidized condition.

* * * * *